(12) United States Patent
Hsieh et al.

(10) Patent No.: US 11,878,067 B2
(45) Date of Patent: Jan. 23, 2024

(54) GEL COMPOSITIONS CONTAINING COPOLYMER OF VINYLPYRROLIDONE AND ACRYLIC ACID

(71) Applicant: L'ORÉAL, Paris (FR)

(72) Inventors: I-Fan Hsieh, Scotch Plains, NJ (US); Ramakrishnan Hariharan, Springfield, NJ (US); Charles Ward, Burlington, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/527,675

(22) Filed: Jul. 31, 2019

(65) Prior Publication Data

US 2021/0030635 A1 Feb. 4, 2021

(51) Int. Cl.
*A61K 8/04* (2006.01)
*A61K 8/81* (2006.01)

(52) U.S. Cl.
CPC ............ *A61K 8/042* (2013.01); *A61K 8/8147* (2013.01); *A61K 8/8176* (2013.01); *A61K 2800/436* (2013.01); *A61K 2800/884* (2013.01)

(58) Field of Classification Search
None
See application file for complete search history.

(56) References Cited

U.S. PATENT DOCUMENTS

| | | |
|---|---|---|
| 7,799,321 B2 | 9/2010 | Botschka et al. |
| 9,655,836 B2 | 5/2017 | Streuli |
| 2006/0084586 A1* | 4/2006 | Drzewinski ............ A61Q 19/00 510/119 |
| 2007/0231286 A1* | 10/2007 | Botschka ................ A61K 8/19 424/63 |
| 2009/0155371 A1 | 6/2009 | Sojka et al. |
| 2011/0097289 A1 | 4/2011 | Viala et al. |
| 2019/0159994 A1 | 5/2019 | Pang et al. |
| 2019/0167556 A1 | 6/2019 | Hsieh et al. |

FOREIGN PATENT DOCUMENTS

| | | |
|---|---|---|
| DE | 10 2005 020 704 A1 | 11/2006 |
| DE | 10 2007 053 957 A1 | 5/2009 |
| EP | 1 712 256 A1 | 10/2006 |
| EP | 2 221 045 A1 | 8/2010 |
| EP | 2 468 238 A2 | 6/2012 |

OTHER PUBLICATIONS

"Straighten Out Straightening Cream" Mintel, 2016, 3 pages.
"Tinted Eye Brow Gel" Mintel, 2012, 3 pages.
"Velvet Crème" Mintel, 2019, 3 pages.
"Choppy Cream WaX" Mintel, 2013, 3 pages.
"Go for Texture Creme Wax" Mintel, 2013, 3 pages.
International Search Report and Written Opinion ofthe International Searching Authority dated Oct. 26, 2020 in PCT/US2020/044146, 16 pages.

* cited by examiner

*Primary Examiner* — Danah Al-Awadi
(74) *Attorney, Agent, or Firm* — WOMBLE BOND DICKINSON (US) LLP

(57) ABSTRACT

Gel compositions including at least one copolymer of vinylpyrrolidone and acrylic acid, at least one film forming agent, and at least one coloring agent, and methods of applying such compositions to keratinous materials, are provided.

19 Claims, No Drawings

US 11,878,067 B2

1

GEL COMPOSITIONS CONTAINING COPOLYMER OF VINYLPYRROLIDONE AND ACRYLIC ACID

FIELD OF THE INVENTION

The present invention relates to gel compositions comprising at least one copolymer of vinylpyrrolidone and acrylic acid, at least one film forming agent, and at least one coloring agent. Among other improved or beneficial properties, these compositions have surprisingly good properties including transfer-resistance and oil-resistance.

DISCUSSION OF THE BACKGROUND

U.S. Pat. No. 7,799,321 discloses compositions containing VP/AA copolymers.

U.S. Pat. No. 9,655,836 discloses using anionic cross-linked rheology-modifying polymers with high molecular weight charged polymers.

US 2011/0097289 discloses polyurethane dispersions for decorative cosmetics which may include thickeners.

EP 2468238 discloses hair fixative that lists numerous polymers for possible inclusion but which requires silicone wax and propellant and does not contain coloring agent.

None of the above references discloses or suggest gel compositions having transfer-resistance properties and oil-resistance properties containing the required ingredients. Thus, there remains a need for such improved compositions having improved cosmetic properties including transfer-resistance and oil-resistance properties.

Accordingly, one aspect of the present invention is a care and/or makeup and/or treatment composition for keratinous materials which has good cosmetic properties such as, for example, good transfer-resistance and oil-resistance, particularly a composition containing a coloring agent.

SUMMARY OF THE INVENTION

The present invention relates to gel compositions comprising at least one copolymer of vinylpyrrolidone and acrylic acid, at least one film forming agent, and at least one coloring agent.

The present invention also relates to methods of treating, caring for and/or making up keratinous materials by applying compositions of the present invention to a keratinous material in an amount sufficient to treat, care for and/or make up the keratinous material.

The present invention also relates to methods of enhancing the appearance of keratinous materials by applying compositions of the present invention to a keratinous material in an amount sufficient to enhance the appearance of the keratinous material.

The present invention also relates to methods of enhancing the appearance of keratinous materials by a primer composition to a keratinous material, and then applying a composition of the present invention to the primer composition in an amount sufficient to enhance the appearance of the keratinous material.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

2

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means any material such as, for example, a polymer or a resin that leaves a film on the substrate to which it is applied.

"Polymer" as used herein means a compound which is made up of at least two monomers.

"Keratinous materials" includes materials containing keratin such as hair, skin, eyebrows, lips and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Long wear" compositions as used herein refers to compositions where the compositions, after application to a keratinous material, do not transfer or smudge after contact with another substrate and retain a consistent appearance on the keratinous material for an extended period of time. "Long wear" compositions, as used herein can also refer to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to keratinous materials such as skin, eyelashes or lips and evaluating the color of the composition after an extended period of time. For example, the color of a composition may be evaluated immediately following application to the keratinous material and these characteristics may then be re-evaluated and compared after a certain amount of time. Further, these characteristics may be evaluated with respect to other compositions, such as commercially available compositions. Additionally, long wear properties may be evaluated by applying a sample, allowing it to dry, and then abrading the sample to determine removal/loss of sample.

"Transfer" as used herein refers to the displacement of a fraction of a composition which has been applied to a keratinous material by contact with another substrate, whether of the same nature or of a different nature. For example, when a composition such as an eyeshadow, eyeliner or mascara has been applied, the composition can be transferred onto hands by rubbing or by contact of the hands with the eyes. By way of further example, when a composition such as a lipstick has been applied, the composition can be transferred onto teeth or hands, or onto the cheek of another person. Irrespective of composition type, the composition can also transfer from the keratinous material to which it has been applied to another substrate such as napkins, collars, glasses, cups or other containers.

"Transfer-resistance" as used herein refers to the quality exhibited by a composition in resisting transfer. To determine transfer-resistance, the amount of composition transferred from a keratinous material to a substrate may be evaluated and compared. For example, a composition may be transfer-resistant if, after application to a keratinous material such as lips, skin or eyelashes and contact with a substrate, a majority of the composition is left on the wearer. Further, the amount transferred may be compared with that transferred by other compositions, such as commercially-available compositions. In a preferred embodiment of the present invention, little or no composition is transferred to the substrate from the keratinous material.

"Oil-resistance" or "sebum-resistance" as used herein means transfer resistance when the composition contacts oil or sebum, respectively.

"Gel Crossover Point (Sol/Gel Point)", means the point at which the G" (loss modulus) intersects the G' (storage modulus), reported in % strain. It is the point at which a composition goes from a more solid state to a more liquid state. An example of a method for determining gel crossover point is as follows: a Discovery HR-2 Rheometer by TA Instruments can be used, having 40 mm parallel plate geometry on a stainless steel flat peltier plate. The test can be run @ 25° C., with test parameter of angular frequency of 1.0 rad/s and logarithmic sweep: Strain % 0.1 to 1000.0%. 5 points per decade.

The compositions and methods of the present invention can comprise, consist of, or consist essentially of the essential elements and limitations of the invention described herein, as well as any additional or optional ingredients, components, or limitations described herein or otherwise useful in personal care.

In accordance with the present invention, gel compositions comprising at least one copolymer of vinylpyrrolidone and acrylic acid, at least one film forming agent, and at least one coloring agent are provided.

According to preferred embodiments, the gel compositions of the present invention have a gel crossover point ranging from about 2% to about 50% strain, preferably from about 3% to about 40% strain, and preferably from about 4% to about 30% strain, including all ranges and subranges therebetween.

Copolymer of Vinylpyrrolidone and Acrylic Acid

In accordance with the present invention, compositions comprising at least one copolymer of vinylpyrrolidone and acrylic acid are provided. Suitable copolymers are described, for example, in U.S. Pat. Nos. 7,799,321 and 7,205,271, the entire contents of both of which are hereby incorporated by reference.

Preferably, the copolymer is crosslinked. Suitable crosslinkers have at least two free radical polymerizable groups in the molecule, e.g. pentaerythritol trial lylether, pentaerythritol triacrylate, pentaerythritol tetraacrylate or methylene bisacrylamide.

Preferably, the copolymer is linear.

According to preferred embodiments, the copolymer comprises about 10-90 wt. % of vinyl pyrrolidone and about 10-90 wt. % of acrylic acid, including all ranges and subranges there between. So, for example, copolymers could include 10%-50% vinylpyrrolidone and 50%-90% acrylic acid; 40%-80% vinylpyrrolidone and 20%-60% acrylic acid; 25%-75% vinylpyrrolidone and 25%-75% acrylic acid; 55%-85% vinylpyrrolidone and 15%-45% acrylic acid; 30%-60% vinylpyrrolidone and 40%-70% acrylic acid, etc.

A suitable example of a commercially-available copolymer of vinylpyrrolidone and acrylic acid is Ultrathix™ P-100 available from Ashland Specialty Company (100% active solid content).

The copolymer of vinylpyrrolidone and acrylic acid is preferably present in the compositions of the present invention in an active solid content amount ranging from greater than 0.1% to about 20%, preferably from greater than 0.5% to about 10%, and preferably from about 1% to about 5%, by weight with respect to the total weight of the composition, including all ranges and subranges there between, such as 1-10%, 2-8%, 1-6%, etc.

Film Forming Agent

In accordance with the present invention, compositions comprising at least one film forming agent are provided. According to preferred embodiments, the film forming agent is selected from the group consisting of (1) polymers including imide group(s), (2) low molecular weight sulfopolyester compounds, and (3) mixtures thereof. Each of these preferred film forming agents will be discussed below. For sake of clarity, it is to be understood that the copolymer of vinylpyrrolidone and acrylic acid can possess film forming properties as well.

Polymer Including Imide Group(s)

According to preferred embodiments, the polymer including imide group(s) is selected from the group consisting of alkylmaleimides, polysuccinimides, and hydroxyalkylmaleimides. Examples of suitable polymers include polymers containing repeating units of alpha-olefin N-alkylmaleimide or alpha-olefin N-hydroxyalkylmaleimide, a specific example of which is isobutylene/ethylmaleimide/hydroxyethylmaleimide copolymer (polyimide-1), which is available in a commercial product sold under the name Aquaflex®FX-64 (30% active solid content in water). Polysuccinimide sold under the name Rhodomer PSI, polysuccinimide partially (50%) modified, and polyisobutylene succinimide sold under the name Hostacerin PIB are other examples of acceptable polymers.

Further examples of suitable polymers as well as methods of producing such polymers can be found in U.S. Pat. Nos. 5,886,194, 5,869,695, and 6,025,501, and PCT patent application WO 9967216, the entire contents of all of which are hereby incorporated by referenced.

Low Molecular Weight Sulfopolyester Compound

As used herein, "sulfopolyester compound" means a polymeric compound made from glycol(s), aromatic diacid(s), phthalic acid(s) and neutralized phthalic acid sulfonates. The sulfopolyester compound may be made from additional monomers in addition to the four identified monomers—that is, the sulfopolyester compound may "comprise" the four identified monomers, or it may "consist essentially of" the four identified monomers. The sulfopolyester compound may also "consist of" only the four identified monomers.

Suitable glycols include, but are not limited to, alkylene glycols and diglycols such as ethylene glycol, propylene glycol, ethylene diglycol and propylene diglycol.

Suitable aromatic diacids include, but are not limited to, cyclohexanedialkanols such as, for example, cyclohexanedimethanol, cyclohexanediethanol, cycloexanedipropanol, cyclohexanedibutanol, cyclohexanediisobutanol, etc., and cyclopentanedialkanols such as, for example, cyclopentanedimethanol, cyclopentanediethanol, etc.

Suitable phthalic acids include, but are not limited to, isophthalic acid and terephthalic acid.

Suitable neutralized phthalic acid sulfonates include, but are not limited to, alkali isophthalic acid sulfonates such as sodium isophthalic acid sulfonates, potassium isophthalic acid sulfonates, etc., and alkali terephthalic acid sulfonates such as sodium terephthalic acid sulfonate and potassium terephthalic acid sulfonate.

As used herein, "low molecular weight" means less than 75,000 Da weight average molecular weight, preferably less than 60,000 Da, preferably less than 50,000 Da, and preferably less than 40,000 Da, including all ranges and subranges therebetween.

According to preferred embodiments, the low molecular weight sulfopolyester compound is polyester-1 or polyester-5, a diethylene glycol/phthalate/isophthalate/1,4-cyclohexanedimethanol copolymer (INCI name: diglycol/CHDM/isophthalates/SIP copolymer) sold under the names Eastman AQ polymer (AQ35S, AQ38S, AQ55S, AQ48 Ultra) by the company Eastman Chemical.

The film forming agent is preferably present in the compositions of the present invention in an active solid content amount ranging from about 0.1% to about 20%, preferably from about 0.2% to about 10%, preferably from about 0.25% to about 5%, and preferably from about 0.33% to about 3%, by weight with respect to the total weight of the composition, including all ranges and subranges there between, such as 1-10%, 2-8%, 1-6%, etc.

According to preferred embodiments, the copolymer of vinylpyrrolidone and acrylic acid and the film forming agent are present in the compositions of the present invention in an active solid content weight ratio of greater than or equal to 1:1, preferably greater than or equal to 1.5:1, preferably greater than or equal to 2:1, and preferably greater than or equal to 3:1, including all ranges and subranges therebetween, such as, for example, 1:1 to 10:1, 2:1 to 0.7:1; and 1.5:1 to 4:1, etc.

According to preferred embodiments, the weight amount of copolymer of vinylpyrrolidone and acrylic acid present in the compositions of the present invention is greater than the weight amount of film forming agent.

Coloring Agents

According to the present invention, gel compositions comprising at least one coloring agent are provided. The coloring agent is preferably chosen from pigments, dyes, such as liposoluble dyes or water-soluble dyes, nacreous pigments, glitter and pearlescent pigments.

Representative liposoluble dyes which may be used according to the present invention include Sudan Red, DC Red 17, DC Green 6, ß-carotene, soybean oil, Sudan Brown, DC Yellow 11, DC Violet 2, DC Orange 5, annatto, and quinoline yellow. The liposoluble dyes, when present, generally have a concentration ranging up to 40% by weight of the total weight of the composition, such as from 0.0001% to 30%, including all ranges and subranges therebetween.

The nacreous pigments which may be used according to the present invention may be chosen from colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.0001% to 40%, preferably from 0.001% to 30%, including all ranges and subranges therebetween.

Pigments may be chosen from white, colored, inorganic, organic, polymeric, and nonpolymeric pigments. Representative examples of mineral pigments include titanium dioxide, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

The coloring agents (colorants) are preferably present in the gel compositions of the present invention in a concentration ranging up to 50% by weight of the total weight of the composition, such as from 1% to 40%, and further such as from 5% to 30%, including all ranges and subranges therebetween such as, for example, 2-25%, 5-35%, 10-40%, etc.

Aqueous Phase

The gel compositions of the present invention also contain water. Water is preferably present in an amount of from about 10% to about 80% by weight, preferably from about 20% to about 70% by weight, preferably from about 35% to about 65% by weight, including all ranges and subranges therebetween, all weights being based on the total weight of the composition.

Fatty Substances

According to certain embodiments of the present invention, compositions further comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |

TABLE 1-continued

| Compound | Flash Point (° C.) | Viscosity (cSt) |
|---|---|---|
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexadecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:
hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearinerie Dubois or those sold under the names Miglyol 810, 812 and 818 by the company Dynamit Nobel;
synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
synthetic ethers containing from 10 to 40 carbon atoms;
$C_8$ to $C_{26}$ fatty alcohols, for instance oleyl alcohol, cetyl alcohol, stearyl alcohol, and cetearyl alcohol; and
mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to certain embodiments, if present, then at least one oil is present in the compositions of the present invention in an amount ranging from about 0.5 to about 30% by weight, preferably from about 1 to about 10% by weight, and preferably from about 1 to about 5% by weight, based on the total weight of the composition, including all ranges and subranges within these ranges.

According to certain embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice bran wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to certain embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di) methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x$ $(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to certain embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

If present, the wax or waxes may be present in an amount ranging from 0.5% to 10% by weight relative to the total weight of the composition, for example from 1% to 10%, and for example from 1% to 5%, including all ranges and subranges therebetween.

According to preferred embodiments, the compositions of the present invention contain less than 1% wax and/or less than 1% oil.

According to preferred embodiments, the compositions of the present invention contain less than 0.5% wax and/or less than 0.5% oil.

According to preferred embodiments, the compositions of the present invention contain no wax and/or oil.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers such as cellulose fibers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9$^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the keratinous materials of human beings such as, for example, lips, skin or eyelashes.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, 2$^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

Also, silica aerogel particles can be added to compositions of the present invention, if desired. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying operations are described in detail in Brinker C. J., and Scherer G. W., Sol-Gel Science: New York: Academic Press, 1990.

Hydrophobic silica aerogel particles which may be used in the present invention can have a specific surface area per unit of mass ($S_M$) ranging from 500 to 1500 m²/g, preferably from 600 to 1200 m²/g and better still from 600 to 800 m²/g, and a size expressed as the volume-average diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles which may be used in the present invention have a size, expressed as volume-average diameter (D[0.5]), ranging from 1 to 30 µm, preferably from 5 to 25 µm, better still from 5 to 20 µm and even better still from 5 to 15 µm.

The specific surface area per unit of mass can be determined by the nitrogen absorption method, known as the BET (Brunauer-Emmett-Teller) method, described in The Journal of the American Chemical Society, vol. 60, page 309, February 1938, which corresponds to international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

According to one advantageous embodiment, the hydrophobic silica aerogel particles which may be used in the present invention have a specific surface area per unit of mass ($S_M$) ranging from 600 to 800 m²/g and a size expressed as the volume-average diameter (D[0.5]) ranging from 5 to 20 µm and even better still from 5 to 15 µm.

The silica aerogel particles which may be used in the present invention may advantageously have a tapped density p ranging from 0.02 g/cm³ to 0.10 g/cm³, preferably from 0.03 g/cm³ to 0.08 g/cm³ and preferably from 0.05 g/cm³ to 0.08 g/cm³.

According to one preferred embodiment, the hydrophobic silica aerogel particles which may be used in the present invention have a specific surface area per unit of volume $S_V$ ranging from 5 to 60 m²/cm³, preferably from 10 to 50 m²/cm³ and better still from 15 to 40 m²/cm³. The specific surface area per unit of volume is given by the relationship: $S_V=S_M\times\rho$, where $\rho$ is the tapped density, expressed in g/cm³, and $S_M$ is the specific surface area per unit of mass, expressed in m²/g, as defined above.

Preferably, the hydrophobic silica aerogel particles which may be used according to the invention have an oil-absorbing capacity, measured at the wet point, ranging from 5 to 18 ml/g, preferably from 6 to 15 ml/g and better still from 8 to 12 ml/g. The absorbing capacity measured at the wet point, noted Wp, corresponds to the amount of oil that needs to be added to 100 g of particles in order to obtain a homogeneous paste. It is measured according to the "wet point" method or the method for determining the oil uptake of a powder described in standard NF T 30-022. It corresponds to the amount of oil adsorbed onto the available surface of the powder and/or absorbed by the powder by measurement of the wet point, described below: An amount m=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted. The oil uptake corresponds to the ratio Vs/m.

The aerogels which may be used according to the present invention are hydrophobic silica aerogels, preferably of silyl silica (INCI name: silica silylate). The term "hydrophobic silica" is understood to mean any silica of which the surface is treated with silylating agents, for example with halogenated silanes, such as alkylchlorosilanes, siloxanes, in particular dimethylsiloxanes, such as hexamethyldisiloxane, or silazanes, so as to functionalize the OH groups with silyl Si—Rn groups, for example trimethylsilyl groups.

According to preferred embodiments, the compositions of the present invention contain less than 1% surfactant.

According to preferred embodiments, the compositions of the present invention contain less than 0.5% surfactant.

According to preferred embodiments, the compositions of the present invention contain no surfactant.

According to preferred embodiments of the present invention, methods of treating, caring for and/or making up a keratinous material by applying compositions of the present invention to the keratinous material in an amount sufficient to treat, care for and/or make up the keratinous material are provided. Preferably, "making up" the keratinous material includes applying at least one coloring agent to the keratinous material in an amount sufficient to provide color to the keratinous material.

According to yet other preferred embodiments, methods of enhancing the appearance of a keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratinous material in an amount sufficient to treat, care for and/or make up the keratinous material, to cover or hide defects associated with keratinous material, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1

The following is an example of a composition of the present invention:

| INGREDIENT | 2023864 |
|---|---|
| ACRYLIC ACID/VP CROSSPOLYMER | 1.5 |
| FILM FORMER | X |
| GLYCOL | 0.7 |
| PIGMENTS (OXIDES) | 0.7 |
| ALCOHOL | 5.7 |
| FILLERS | 2.2 |
| OTHER INGREDIENTS | 1.0 |
| WATER | QS |

Example 2—Testing

The composition in example 1 was used as a base composition, and various amounts of film forming agent were added to this base composition to produce different compositions (as reflected in the Tables below). These compositions were tested for oil-resistance and adhesion using the following protocols:

Oil-Resistance Protocol: Use a 3 ml drawdown bar to drawdown the composition on abrasion paper. Let it dry for 24 hours. After drying, put a drop of artificial sebum on top of it, wait for 5 minutes and use kimwipe to wipe it back and forth 5 time and evaluate the amount of composition transferred on the kimwipe as well as the residual of the drawdown on the paper.

Adhesion Protocol: Press a piece of pressure-sensitive tape on the drawdown film and quickly remove the tape. The adhesion was rated by the amount of the composition be removed by the tape. The tape used in the adhesion test is ASTM D3359 cross hatch adhesion test tape.

These properties were evaluated using a numerical rating on a scale of 1-5, where 5=least transfer/best adhesion/best film property and 1=most transfer/worst adhesion/worst film property.

The compositions tested and the results obtained are reproduced in the Tables below:

Comparative Compositions (No Film Former)

| ACRYLIC ACID/VP CROSSPOLYMER (%) | Oil Resistance | Adhesion |
|---|---|---|
| 1% | 4-5 | 1 |
| 1.5% | 4 | 1 |
| 2.5% | 5 | 1 |
| 3.5% | 5 | 1 |

Invention Compositions

| 1.5% ACRYLIC ACID/VP CROSSPOLYMER (%) + Film Former (%) | Oil Resistance | Adhesion |
|---|---|---|
| Polyimide-1 (0.6%) | 5 | 2 |
| Polyimide-1 (1.5%) | 5 | 4 |
| Polyimide-1 (2.4%) | 4-5 | 3 |
| Eastman AQ polymer (0.4%) | 5 | 4-5 |
| Eastman AQ polymer (0.8%) | 5 | 5 |

What is claimed is:

1. A gel composition comprising water, alcohol, at least one copolymer of vinylpyrrolidone and acrylic acid, at least one coloring agent, and at least one film forming agent which is polyimide-1, wherein the polyimide-1 is present in the composition in an active solid content amount ranging from about 0.25% to about 5% by weight with respect to the total weight of the composition,
wherein the composition has a gel crossover point ranging from about 2% to about 50% strain, as measured at 25° C., with a test parameter of angular frequency of 1.0 rad/s, wherein, if surfactant is present, the composition contains less than 0.5% surfactant, and wherein the composition is free of alcohol wax.

2. The composition of claim 1, wherein the at least one coloring agent is a pearlescent pigment.

3. The composition of claim 1, further comprising at least one low molecular weight sulfopolyester compound.

4. A gel composition comprising water, alcohol, at least one crosslinked, linear copolymer of vinylpyrrolidone and acrylic acid, at least one pigment, and at least one film forming agent which is polyimide-1, wherein the polyimide-1 is present in the composition in an active solid content amount ranging from about 0.25% to about 5% by weight with respect to the total weight of the composition and, wherein a weight amount of copolymer of vinylpyrrolidone and acrylic acid present in the composition is greater than a weight amount of polyimide-1, and
wherein the composition has a gel crossover point ranging from about 2% to about 50% strain, as measured at 25° C., with a test parameter of angular frequency of 1.0 rad/s, wherein, if surfactant is present, the composition contains less than 0.5% surfactant, and wherein the composition is free of alcohol wax.

5. The composition of claim 4, wherein the at least one pigment is a pearlescent pigment.

6. The composition of claim 1, wherein the copolymer of vinylpyrrolidone and acrylic acid and the polyimide-1 are present in an active solid content weight ratio of greater than or equal to 1.5:1.

7. The composition of claim 4, wherein the copolymer of vinylpyrrolidone and acrylic acid and the polyimide-1 are present in an active solid content weight ratio of greater than or equal to 1.5:1.

8. The composition of claim 1, wherein the copolymer of vinylpyrrolidone and acrylic acid and the polyimide-1 are present in an active solid content weight ratio of greater than or equal to 3:1.

9. The composition of claim 4, wherein the copolymer of vinylpyrrolidone and acrylic acid and the polyimide-1 are present in an active solid content weight ratio of greater than or equal to 3:1.

10. A method of making up a keratinous material comprising applying the composition of claim 1 to a keratinous material.

11. A method of making up a keratinous material comprising applying a primer composition to the keratinous material, and then applying the composition of claim 1 to the primer composition.

12. A method of making up a keratinous material comprising applying the composition of claim 4 to a keratinous material.

13. A method of making up a keratinous material comprising applying a primer composition to the keratinous material, and then applying the composition of claim 4 to the primer composition.

14. The composition of claim 1, wherein no surfactant is present in the composition.

15. The composition of claim 1, wherein the composition has a gel crossover point ranging from about 3% to about 40% strain.

16. The composition of claim 4, wherein the composition has a gel crossover point ranging from about 3% to about 40% strain.

17. The composition of claim 1, wherein the copolymer of vinylpyrrolidone and acrylic acid and the polyimide-1 are present in an active solid content weight ratio of greater than or equal to 1:1.

18. The composition of claim 1, wherein the polyimide-1 is present in the composition in an active solid content amount ranging from about 0.33% to about 3% by weight with respect to the total weight of the composition.

19. The composition of claim 4, wherein the polyimide-1 is present in the composition in an active solid content amount ranging from about 0.33% to about 3% by weight with respect to the total weight of the composition.

* * * * *